(12) United States Patent
Statham et al.

(10) Patent No.: US 8,222,598 B2
(45) Date of Patent: Jul. 17, 2012

(54) METHOD FOR QUANTITATIVE ANALYSIS OF A MATERIAL

(75) Inventors: Peter John Statham, Bucks (GB); Ian Richard Barkshire, Cambs (GB)

(73) Assignee: Oxford Instruments Analytical Limited, London (GB)

( * ) Notice: Subject to any disclaimer, the term of this patent is extended or adjusted under 35 U.S.C. 154(b) by 47 days.

(21) Appl. No.: 12/452,040

(22) PCT Filed: Jun. 20, 2008

(86) PCT No.: PCT/GB2008/002124
§ 371 (c)(1),
(2), (4) Date: Mar. 1, 2010

(87) PCT Pub. No.: WO2008/155560
PCT Pub. Date: Dec. 24, 2008

(65) Prior Publication Data
US 2011/0129066 A1   Jun. 2, 2011

(30) Foreign Application Priority Data
Jun. 21, 2007 (GB) ................................ 0712052.0

(51) Int. Cl.
*G01N 23/00* (2006.01)
(52) U.S. Cl. ......... 250/306; 250/305; 250/307; 250/310
(58) Field of Classification Search .......... 250/305, 250/306, 310, 311
See application file for complete search history.

(56) References Cited

U.S. PATENT DOCUMENTS

| | | | | |
|---|---|---|---|---|
| 3,742,214 | A | * | 6/1973 | Helmer et al. ............. 250/305 |
| 4,179,604 | A | * | 12/1979 | Christou ................. 250/305 |
| 4,559,450 | A | | 12/1985 | Robinson et al. |
| 4,962,306 | A | * | 10/1990 | Hodgson et al. ........... 250/310 |
| 5,408,098 | A | * | 4/1995 | Wells ................... 250/310 |
| 5,869,833 | A | * | 2/1999 | Richardson et al. ........ 250/310 |
| 6,326,619 | B1 | * | 12/2001 | Michael et al. ........... 250/310 |

(Continued)

FOREIGN PATENT DOCUMENTS

JP     2004022318 A     1/2004

OTHER PUBLICATIONS

Jung et al.: "Coagulation of humic substances and dissolved organic matter with a ferric salt: An electron energy loss spectroscopy investigation" Water Research, Elsevier, Amsterdam, NL, vol. 39, No. 16, (Oct. 1, 2005); pp. 3849-3862, XP005081218; ISSN: 0043-1354.

(Continued)

*Primary Examiner* — Jack Berman
*Assistant Examiner* — Jason McCormack
(74) *Attorney, Agent, or Firm* — Blank Rome LLP

(57) ABSTRACT

A method and apparatus for quantitative analysis of a material in which an electron beam is caused to impinge upon the material are described. The method comprises detecting low loss electrons (LLEs) received from a first region of the material due to interaction with the electron beam and generating corresponding LLE data. The method further comprises detecting x-rays received from a second region of the material due to interaction with the electron beam and generating corresponding x-ray data, wherein the first and second regions overlap, and analysing the LLE data together with the x-ray data so as to generate compositional data representative of the composition of the first region.

15 Claims, 10 Drawing Sheets

U.S. PATENT DOCUMENTS

| | | | |
|---|---|---|---|
| 6,730,907 B1 * | 5/2004 | Feuerbaum et al. | 850/9 |
| 6,835,931 B2 * | 12/2004 | Wright et al. | 250/307 |
| 7,573,031 B2 * | 8/2009 | Behar et al. | 250/310 |
| 2004/0183012 A1 * | 9/2004 | Yaguchi et al. | 250/306 |
| 2005/0173632 A1 * | 8/2005 | Behar et al. | 250/311 |
| 2006/0049349 A1 * | 3/2006 | Shemesh | 250/310 |
| 2006/0291619 A1 * | 12/2006 | Statham | 378/45 |

OTHER PUBLICATIONS

Jung et al; "2.3 Transmission electron microscopy"; Water Research, Elsevier, Amsterdam, NL, vol. 39, No. 16, (Oct. 1, 2005); Part on p. 3851.

Gutierrez-Sosa A Et al.: "Local investigation of electronic structure modulation in BaPb xBil-x03 via highly spatially resolved low-loss electron energy loss spectroscopy" Design and Nature—Design and nature II: Comparing Design in Nature with Science and Engineering 2004 Witpress US, vol. 6, 2004, pp. 537-540, XP002498618 (whole document).

Pratt Et al.; "Quantitative interpretation of the low-loss electron signal" Surface Science, Noth-Holland Publishing Co., Amsterdam, NL, vol. 601, No. 8, Apr. 12, 2007) pp. 1804-1812, XP022026045; ISSN: 0039-6028; Part "2 Experimental" on p. 1805.

* cited by examiner

METHOD FOR QUANTITATIVE ANALYSIS OF A MATERIAL

FIELD OF THE INVENTION

The present invention relates to a method of quantitative analysis of a material, in particular using an electron beam technique. A corresponding apparatus is also provided. The invention finds particular application in scanning electronic microscopes (SEM) and provides a means to achieve a high spatial resolution analysis of the specimen by combining information from x-rays and electrons.

BACKGROUND TO THE INVENTION

Scanning electron microscopes (SEMs) are common tools for the observation of small features. In this technique, a finely focused electron beam ("probe") with an energy typically between about 1 keV and 20 keV is scanned across the surface of a sample. At each probe position on the surface, signals are conventionally measured by a number of different types of detector. Commonly, scattered electrons and x-rays are detected and for each signal, magnified images of the specimen are constructed where the signal strength modulates the intensity at positions corresponding to the probe positions scanned on the surface. At each probe position, the energy spectrum of the scattered electrons and x-rays is determined by the composition and topography of the sample surface and the underlying bulk material. At present compositional analysis in SEMs is most commonly achieved with x-ray detection.

U.S. Pat. No. 4,559,450 describes an analytical technique that makes use of the fact that the total intensity of backscattered electrons (BE) is affected by the atomic number of the specimen. Backscattered electrons are high-energy electrons which are back-scattered from the specimen as a result of its interaction with the beam. Whilst it is secondary electrons rather than backscattered electrons that are used in many imaging applications, backscattered electrons are advantageous since their energy can be analysed so as to obtain some information upon the composition of the part of the material with which the electron beam interacts.

If the BE signal intensity is compared to the intensity from a reference material for the same incident beam current, it is possible to decide if the specimen has an effective atomic number higher or lower than the reference material. A calibration curve can be constructed from a series of reference materials so that the effective atomic number of an unknown specimen can be determined from the BE signal intensity. Furthermore, the effective atomic number for backscattered electrons can be predicted from the chemical composition so that the observed signal can be used to corroborate a "guessed" composition for the material. The guessed composition can be obtained by using x-ray analysis of the specimen to provide information on relative elemental concentrations.

One of the problems of analysis with electrons is that energetic electrons scatter within the specimen and penetrate below the surface. Therefore, x-rays are generated throughout the region reached by the electrons. For example a 15 keV incident beam generates Si K x-rays from a depth of about 3000 nm in pure silicon and a lateral range of a similar dimension. Therefore in these conditions, spatial resolution of analytical information from x-rays is of the order of 3000 nm. For example FIG. 1 shows a 1000 nm diameter particle 10 of silicon on top of a carbon substrate 11 and shows that many electrons reach the substrate where they will generate x-rays that are not representative of the particle. Within FIG. 1, the incident focussed electron beam is shown at 1. Electrons which are scattered back out into the vacuum as backscattered electrons (BE) are shown at 2. X-rays are generated from the electron trajectories within the particle 10, these being illustrated at 3. The electron trajectories within the substrate 11 generate x-rays from the substrate. The electrons are scattered out of the particle 10 so that the x-ray signal is a combination of the signal from the particle 10 and the signal from the substrate 11. Note that in FIG. 1, the vertical scale is in micrometre units.

To contribute to the BE signal, electrons have to scatter backwards out of the specimen and reach a BE detector. Most of these electrons come from depths less than 1000 nm and from a similar lateral range. Therefore, in these conditions, the analytical information provided by the BE signal has a spatial resolution of the order of 1000 nm. As in the case of x-ray analysis, if an object is smaller than the analytical spatial resolution, then the signal generated by the object will not be truly representative of the object material. Therefore, the method based on backscattered electrons described by U.S. Pat. No. 4,559,450 would typically not be suitable to analyse objects much smaller than 1000 nm in dimension using 15 keV incident electrons.

U.S. Pat. No. 6,753,525 recognises that, for small objects, the BE count will depend on the physical dimension of the object being studied and uses a look-up table showing the normalised backscattered electron count as a function of both effective atomic number of the material and the physical dimension of the object being studied. U.S. Pat. No. 6,753,525 also recognises that the high energy of the incident electron beam causes x-rays to emanate from the areas surrounding the features of interest and the size of the region emitting x-rays is considerably larger than for the region producing backscattered electrons. Consequently, the resulting x-ray spectrum cannot be corrected for feature size using a table of correction factors and there is no provision for identifying chemical elements in U.S. Pat. No. 6,753,525. Furthermore, U.S. Pat. No. 6,753,525 makes no reference to the effect of the substrate beneath a small object on the observed BE signal. If the object is partially transparent to incident electrons then the total BE signal will depend on the both the material of the object, the dimensions of the object and the material of the substrate beneath.

For a practical implementation of U.S. Pat. No. 6,753,525 it is likely that the substrate is silicon because the application is to analyse small objects on a semiconductor wafer, which is commonly silicon. However, if the substrate were changed, the lookup table relating BE signal to object dimensions would have to be modified to compensate for the different electron scattering properties of a substrate other than silicon, this requiring significant additional effort.

In both U.S. Pat. No. 4,559,450 and U.S. Pat. No. 6,753,525 the total BE signal is used for characterisation. The BE detectors used in SEMs are typically solid state detectors, scintillator/photomultiplier detectors and micro-channel plate detectors and are used in "analog" mode where there is a continuous readout of the aggregate current liberated in the detector. In a solid state detector, the charge liberated by a single electron striking the detector is roughly proportional to the energy of the incident electron and therefore the total measured current will not only depend on the rate of backscattered electrons hitting the detector but also the spectral distribution of the backscattered electrons. Similarly, all types of BE detector based on electrical current measurement produce a result that depends to some extent on the energy spectrum of incident electrons as well as the count rate of incident electrons. In order to calculate the theoretical expected BE signal from a material, it is therefore necessary to characterise the exact energy response of the BE detector. When there are no electrons hitting the detector, the detector electronics registers an offset current and this may vary with time. Therefore, for any calibration method it is important to compensate for the offset current prior to each measurement. Furthermore, the measured current also depends on the gain of the electronic amplification system and this may vary. The energy dependence of detectors, variation in offset current and variation in gain make characterisation of materials by backscattered electrons difficult in practice.

There are therefore a number of problems associated with the use of backscattered electrons and x-ray techniques in obtaining compositional information, particularly where analysis is needed of objects having small dimensions, such as less than 1000 nanometres.

SUMMARY OF THE INVENTION

In accordance with a first aspect of the present invention we provide a method for quantitative analysis of a material in which an electron beam is caused to impinge upon the material, the method comprising: detecting low loss electrons (LLEs) received from a first region of the material due to interaction with the electron beam and generating corresponding LLE data, detecting x-rays received from a second region of the material due to interaction with the electron beam and generating corresponding x-ray data, wherein the first and second regions overlap, and analysing the LLE data together with the x-ray data so as to generate compositional data representative of the composition of the first region.

We have realised that low loss electrons (LLEs) can be used to great advantage in obtaining compositional information for very small dimension objects (those having at least one, possibly two or three dimensions each preferably less than 1000 nm and more preferably less than 100 nm). This is because the use of LLEs provides a very small interaction volume (first region) with the electron beam, and it is therefore possible to obtain information from such a small volume and use this, together with obtained x-ray information from the larger interaction volume (second region) caused by the trajectories of other electrons, so as to provide information concerning the composition of the small LLE interaction volume, this being the "first region".

In the context of the present invention, LLEs can be defined as electrons that have an energy which is close to the incident beam energy which means that in interacting with the material they have only lost a small amount of energy. In traversing material, electrons lose energy at a rate that depends on the material and the electron energy. A higher atomic number material or a lower incident beam energy gives a greater rate of energy loss. In a typical case, if the rate of energy loss is 10 eV per nm then LLEs that have lost less than 500 eV must have traveled no more than 50 nm in the material and it is the maximum loss energy that governs the size of the region that produces the LLE signal. The region producing the LLE signal will only be substantially smaller than the region producing the total BE signal if the fractional energy loss is limited to a small fraction of the incident beam energy. Therefore for the purpose of the present invention LLEs have a maximum energy that is least 80% of the incident beam energy.

In our invention, rather than use the total BE signal, we use a detector with energy filtering so that only electrons that have lost a small fraction of their energy are detected. Electrons that are backscattered out of the specimen in the early stage of the electron trajectory near the surface will have energies close to the primary beam energy and are thus "low loss electrons" (LLEs). These LLEs produce a signal that arises from a shallow region that is close to the incident beam. For example, if incident electrons at 15 keV strike a pure Si specimen, then most electrons that have lost less than 500 eV in energy will emerge from depths and spatial extent of the order of 100 nm. Therefore, by using energy filtering, the LLE signal can be representative of much smaller objects than the total BE signal and there is no need to use a look up table to correct for the size of the object and no need to compensate for the effect of the substrate.

The first region can therefore be thought of as that from which the LLEs are obtained. The first region is therefore typically substantially smaller in volume than the second region and is also contained within it. In the analysis step, the LLE data are typically processed so as to obtain an effective atomic number which is representative of the element or elements within the first region. This can be achieved using a series of known materials to prepare a calibration curve for example. This technique can therefore be thought of as analogous to U.S. Pat. No. 4,559,450 although typically in the creation of such a calibration curve, unlike in U.S. Pat. No. 4,559,450, energy filtering is used to ensure that only LLEs are processed by excluding all electrons that have lost more than a certain threshold energy. Preferably a detector is used that counts individual electrons, rather than measuring the aggregate current produced in a transducer within the detector. By using discrete counting of electrons in a "pulse mode" detection process, the problems of variable conversion efficiency, variable offset current and variable gain that plague "analogue" or continuous mode detection systems, are avoided. An example of such a calibration curve is shown in FIG. 2.

FIG. 2 provides an example calibration curve for 10 keV incident electrons. The LLE signal is collected from backscattered electrons that have energies in excess of 8 keV, therefore having a 2 keV maximum loss, and the number of detected electrons is then expressed as a fraction of the incident electrons that have struck the specimen. In practice, a method is used for calibration where some consistent measure of the LLE signal is expressed as a ratio to some consistent measure of the incident beam current to provide a normalised LLE signal that is independent of beam current. A number of pure element specimens, each with a different atomic number Z, may be used to obtain points upon the calibration curve. When an unknown specimen is exposed to the 10 keV beam, the normalised LLE signal can be converted into an effective Z value. Even though the specimen may be composed of several elements, the LLE signal is thus converted into an effective atomic number or effective Z which is the atomic number of a pure single element material that would give the same LLE signal as the multielement specimen.

The effective Z of a pure single element material that would give the same LLE signal intensity as the compound can alternatively be calculated from physical theory using the concentrations of the constituent elements, for example using simple approximations as described in U.S. Pat. No. 4,559, 450.

In the case of a compound, where the elements are known but the relative concentrations are unknown, the LLE signal effectively provides one mathematical equation relating the set of unknown concentrations to the measured LLE signal.

Typically therefore the LLE data are processed so as to identify which possible combinations of elements are present within the first region for which the theoretical calculation would give the same effective atomic number as measured from the LLE signal. In most cases when attempting to determine the composition of the first region, a number of materials are identified as possible candidates for the material of the first region. Typically the method comprises selecting a candidate material from a number of possible candidate materials for the first region, based upon the LLE data. Each of such candidate materials will have an effective atomic number substantially the same as that obtained from the calibration curve for example.

If the electron detector is capable of measuring the intensity in a series of energy bands near to the beam energy, additional information on composition can be determined from the ratio of intensities in these bands (see for example: "Reflected electron energy loss microscopy (REELM) studies of metals, semiconductors and insulators", E. Paparazzo Journal of Electron Spectroscopy and Related Phenomena 143 (2005) 219-231). This provides an additional or alternative method for selecting candidate materials.

Although analytical information can be obtained with high spatial resolution using LLE, there is no detail of elemental content in the LLE signal. In contrast, the x-ray spectrum stimulated by electrons scattered within the specimen reveals information on the chemical elements present but the information volume is much larger than that for the LLE signal.

Reference is now made to FIG. 3 which shows the first region 15 and second region 16. Electrons that have lost only a small amount of energy will have only interacted with the small hatched region 15 (first region). Thus the LLE information volume has a spatial extent close to that of the focussed incident electron beam. X-rays are generated all the way along the trajectories of electrons that penetrate and scatter within the specimen as a whole. Thus the x-ray information volume shown as the second region 16, typically has much larger dimensions than that of the focussed electron beam 1.

Even though the second region is typically substantially larger than the first region, the information obtained from the second region can be used to reduce the list of possible candidate materials. For example, in order to achieve this, the method may further comprise calculating simulated x-ray data for the candidate material in question, the simulated x-ray data being that which is received only from the first region. This may be achieved by assuming the presence of only a film of material from the first region which has substantially the same thickness as the first region. Thereafter, the simulated x-ray data and the x-ray data obtained from the physical measurement can be compared so as to determine which elemental contributions to the measured x-ray data of the first region are actually detectable within that x-ray data.

The method can therefore be repeated for a number of different selected candidate materials so as to form a set of candidate materials having corresponding compositional data wherein, if one or more elemental contributions should be detectable that are not present within the x-ray data for a particular candidate material, then the said particular candidate material is not included within the set. Thus the set of candidate materials can be significantly smaller in number than those selected using the LLE data alone. In many cases, the set may be reduced to a single candidate material.

In an alternative method, which avoids the need for producing simulated x-ray data, the x-ray data are analysed so as to identify elements present within the second region. A number of candidate materials are selected for the first region based upon the LLE data, each candidate material comprising one or more elements. Thereafter a comparison is performed so as to identify common elements between those identified from the x-ray data and those within each candidate material. The candidate materials are then ranked in accordance with the comparison.

For example, if a candidate material has three elements, each of which is also identified in the x-ray data, then this may be given a ranking of "3". If only two such elements are found within the x-ray data then a ranking of "2" is awarded, and so on. This therefore provides a faster and yet more simple method of selecting a set of candidate materials using the LLE data and x-ray data.

It will further be appreciated that the invention is not limited to the analysis being performed at a specific location upon the material with respect to the beam position. Typically, the method further comprises causing relative movement between the electron beam and the material so as to obtain LLE data and x-ray data for a number of different locations wherein the analysis method is performed at each said location. This may be conveniently achieved in a scanning electron microscope, although other electron microscopes could be used. The different locations may therefore be arranged to collectively form a field of view region wherein the method further comprises forming image data representative of the compositional data at each location. It is further recognised that the information obtained may be used in addition to other information obtained from the use of the electron beam. For example the method may further comprise, for each location, obtaining additional backscattered electron data from electrons which are not low loss electrons and processing the backscattered electron data to obtain further compositional information. This further compositional information may be combined with the image data so as to generate enhanced imaged data, this for example showing additional features or additional composition information within the image.

Although not essential, the method typically comprises the further step of displaying the image to a user.

Whilst the invention lends itself to the analysis of small objects, it is also recognised herein that such objects may indeed comprise layers within a material.

In the event that the material comprises a plurality of layers and these are arranged such that the incident electron beam is approximately parallel to the surfaces of the layers, then the method may further comprise the steps of, iteratively:

i) defining composition data for each layer;
ii) using the composition data to calculate the effective atomic number for each layer;
iii) simulating the x-ray emission as simulated x-ray data from at least one electron beam position for each layer;
iv) detecting the low loss electrons and x-rays for each electron beam position;
v) comparing the detected and simulated x-ray data;
vi) calculating an effective atomic number based upon the detected LLE data;
vii) comparing the calculated effective atomic number in step (v) with that of step (ii);
viii) adjusting the composition data and repeating steps (i) to (vii) using the adjusted composition data as the defined composition data, until the difference between the results of each comparison reaches a predetermined threshold.

This iterative technique allows the composition of the multi-layer specimen to be determined. Typically a figure of merit is used as a numerical measure of the outcome of the comparison steps, this figure of merit being typically maximised or optimised so as to converge the process upon the most likely solution.

It is also possible that the incident electron beam may be arranged approximately normal to the layers, such that it is incident upon a first layer of the plurality of layers, the other layers nevertheless falling within the second region. The method may therefore be used to obtain a composition of the first layer which in turn can provide information in addition to that available by other techniques, so as to allow the structure as a whole in terms of its composition and layer thicknesses to be determined.

As will be appreciated, the compositional information typically comprises the identity of each of the elements within the material within the first region, together with their relative quantities.

The analytical information from LLE can be used to provide detailed information from shallow depths and demarcate the spatial extent of material of different composition. This additional information can be used to resolve analytical problems where the low spatial resolution and higher depth information from an x-ray detector is insufficient to locate fine scale variation in material composition.

In accordance with a second aspect of the present invention we provide apparatus for performing quantitative analysis of a material, the apparatus comprising:— an electron beam generator which in use causes an electron beam to impinge upon a sample of the material;

a low loss electrons (LLEs) detector positioned so as to receive and detect low loss electrons from a first region of the material due to interaction with the electron beam, the low loss electrons detector producing a corresponding LLE signal;

an x-ray detector positioned so as to receive and detect x-rays from a second region of the material due to interaction with the electron beam, the x-ray detector producing a corresponding x-ray signal; wherein the first and second regions overlap; and, a processor adapted to analyse LLE data representative of the LLE signal, together with x-ray data representative of the x-ray signal, so as to generate compositional data representative of the composition of the first region.

As has been discussed, the invention lends itself to use within an electron microscope and therefore preferably the apparatus comprises an electron microscope, typically a scanning electron microscope (SEM). Preferably a low loss electron detector is used, which differs from a standard scattered electron detector in that only low loss electrons are analysed, and in that, typically, individual low loss electrons are counted rather than there being a measurement of the aggregate electrical current produced as a result of a plurality of received electrons. Thus the low loss electron detector is preferably operated in a pulse mode during use where each incident electron generates a pulse output with magnitude dependent on energy and gain and a suitable threshold is used to detect a pulse so that a single count is recorded for each incident electron, irrespective of energy and gain. It will be appreciated that the apparatus is preferably used for the performance of the method according to the first aspect.

It will further be appreciated that it is not essential that the apparatus itself contains the processor for performing the analysis. Typically this may be achieved using a computer which operates the electron beam apparatus in question, such as an SEM computer. However, it is of course feasible that the processing of the data may be achieved remotely, for example over any network capable of carrying the x-ray and LLE data.

Thus, the invention provides a method to deliver quantitative analytical information in apparatus such as a SEM at much higher spatial resolution than can be achieved by x-ray analysis or conventional backscattered electron compositional analysis. Furthermore, analytical information is obtained for material at depths much shallower than that achieved by x-ray analysis or backscattered electron compositional analysis.

BRIEF DESCRIPTION OF THE DRAWINGS

Some examples of the use of a method and apparatus in accordance with the present invention are now described with reference to the accompanying drawings, in which:—

DETAILED DESCRIPTION OF EXAMPLES

A number of different example applications of the invention are now described which provide material identification at high spatial resolution. The invention uses x-ray and LLE analysers, processing the data from each so as to achieve significant advantages over prior art techniques.

Example 1

Figure 4A:
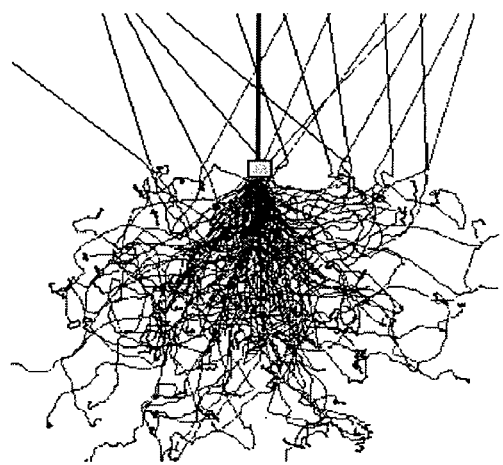
FIGS. 4a, 4b, 4c illustrate the technique for calculating whether x-rays from the first region are detectable.
Figure 4B:
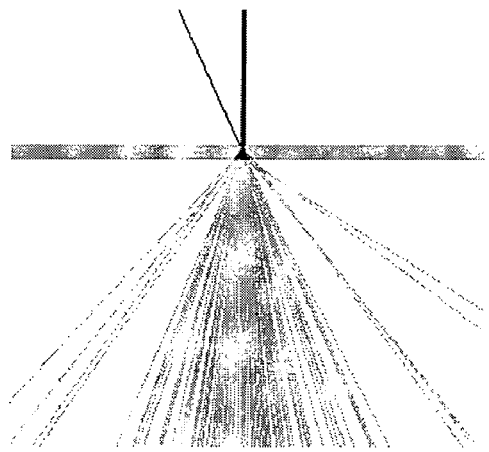
Figure 4C:
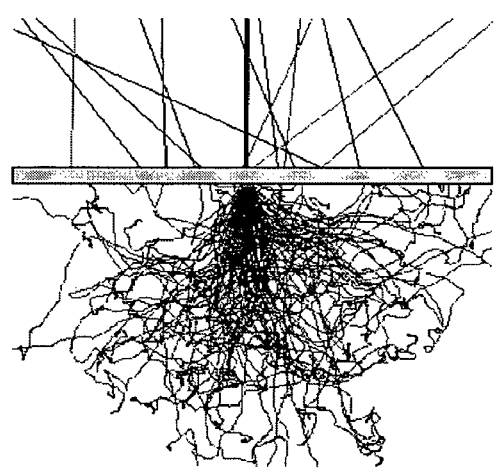

This first example describes a method of combining LLE and x-ray data to identify the material of an object that is smaller than the x-ray excitation volume (the second region). FIGS. 4a, 4b and 4c show a cross section through a specimen to illustrate electron trajectories that produce the LLE and x-ray signals. The smaller the electron energy loss, the smaller the information volume for the LLE signal (the first region). For example, for an energy loss of 100 eV or less, the information volume is typically of the order of 10 nm across. If there is a small object embedded in the surface and bigger than 10 nm across, the LLE signal would be representative of the material constituting this small object. This is shown in FIG. 4a where it should be noted that the focussed electron beam diameter is less than 10 nm. However, x-rays are emitted all along the electron trajectories (within the second region) so the x-ray spectrum is representative of material from both the small object and the surrounding matrix material. If the elemental composition of the object is known, it is possible to calculate a conservative estimate of the intensity of each of the elemental emission lines by calculating the x-ray yields for a thin film of the same material as the object in the first region, held in vacuum. This is shown in FIG. 4b. The thickness of this hypothetical film is set to the depth of the first region, that is, the region from which the selected LLEs are obtained (this can be seen by comparing FIGS. 4a and 4b). For small depths, the excited volume of material will be no greater than that of the small object.

The estimate is calculated as simulated x-ray data for this hypothetical thin film. The estimate is conservative because in practice there is material beneath the object and scattered electrons from underneath add to the excitation. This is shown in FIG. 4c.

Furthermore, if the object were bigger than the LLE information volume, then the x-ray signal for each of the elements would be larger. The total x-ray spectrum obtained from the specimen of FIG. 4a will have peaks corresponding to elemental line emissions and will exhibit statistical counting effects. The ability to detect a small elemental peak will be determined by the size of the peak and the count level for the underlying bremsstrahlung background and nearby overlapping peaks.

The LLE signal represents material that is close to the finely focussed electron probe and has an information volume much less than the volume for x-ray generation. The LLE signal would be the same whether the material was concentrated in a small object or covered the whole surface of the specimen. The X-ray signal intensity for each element for a small object on a substrate (FIG. 4a) will be no less than the intensity for a free standing layer of the same material (FIG. 4b). If the composition of a candidate material is known, then calculated element line intensities for the FIG. 4b arrangement and the observed total spectrum counting statistics from the FIG. 4a arrangement can be used to see what element line signals would definitely be detected in the x-ray spectrum if the object were made of this material. If the object were larger than in FIG. 4a, the intensities would be even greater than in FIG. 4b.

The simulation, detection and signal processing associated with x-ray analysis are well established techniques and therefore we do not discuss these further here.

Using the measured spectrum from the real specimen and the simulated (underestimate) of the elemental line intensities, it is possible to find out how many of the elements present in a candidate material should be detected in the spectrum if the small object were made of that material.

If these elements should be detected, but are not detected, then that candidate material can be excluded from consideration.

Figure 2:
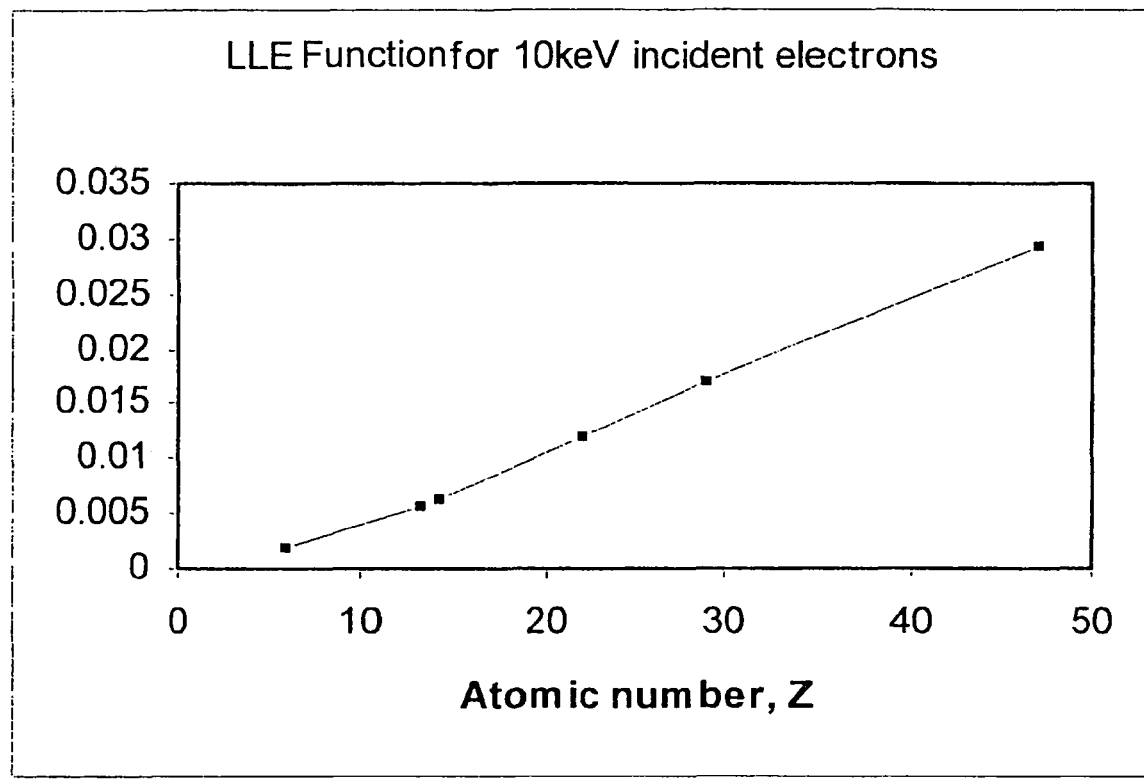
FIG. 2 is a calibration curve relating LLE function to atomic number.
Figure 3:
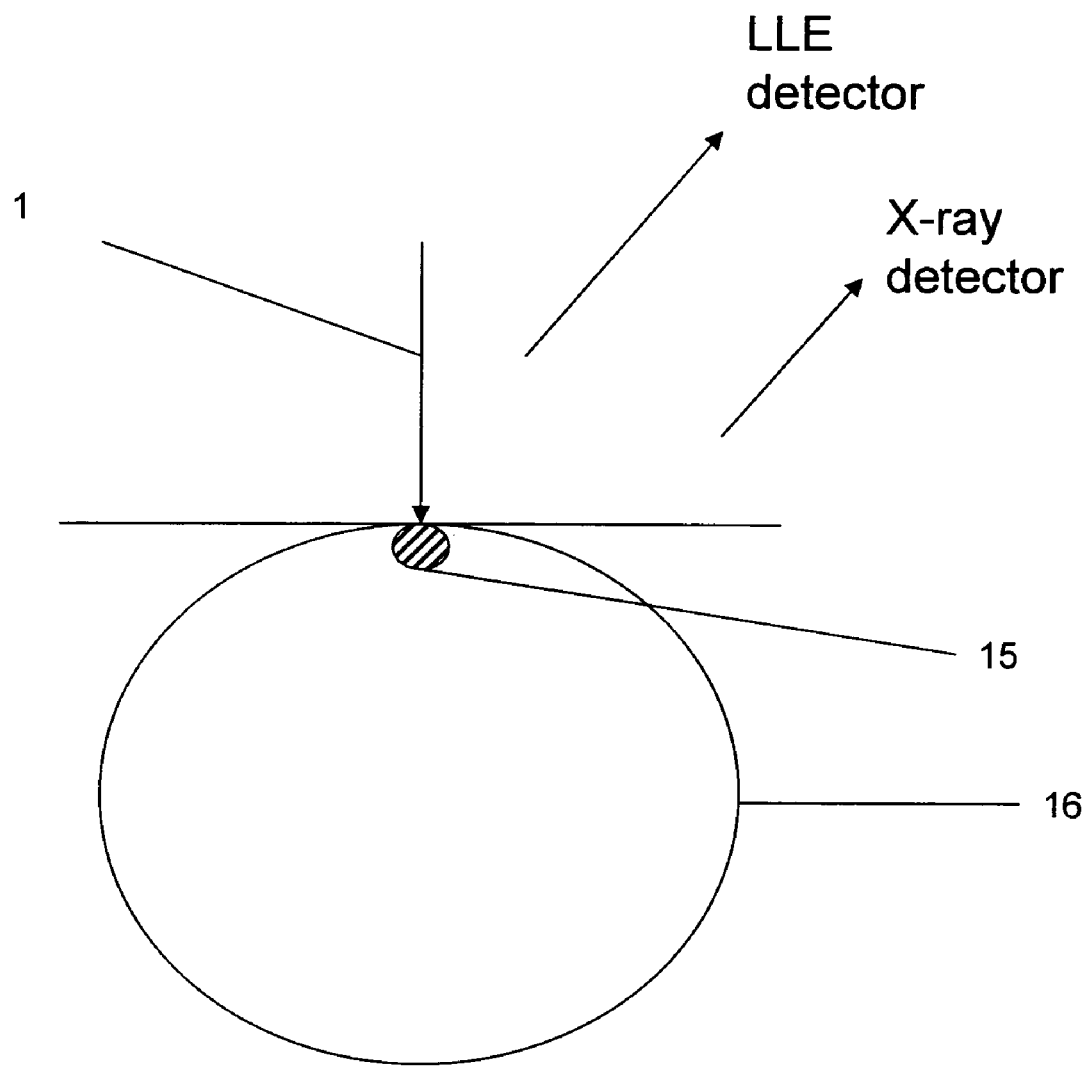
FIG. 3 is a schematic representation of the first and second interaction regions.
Figure 5:
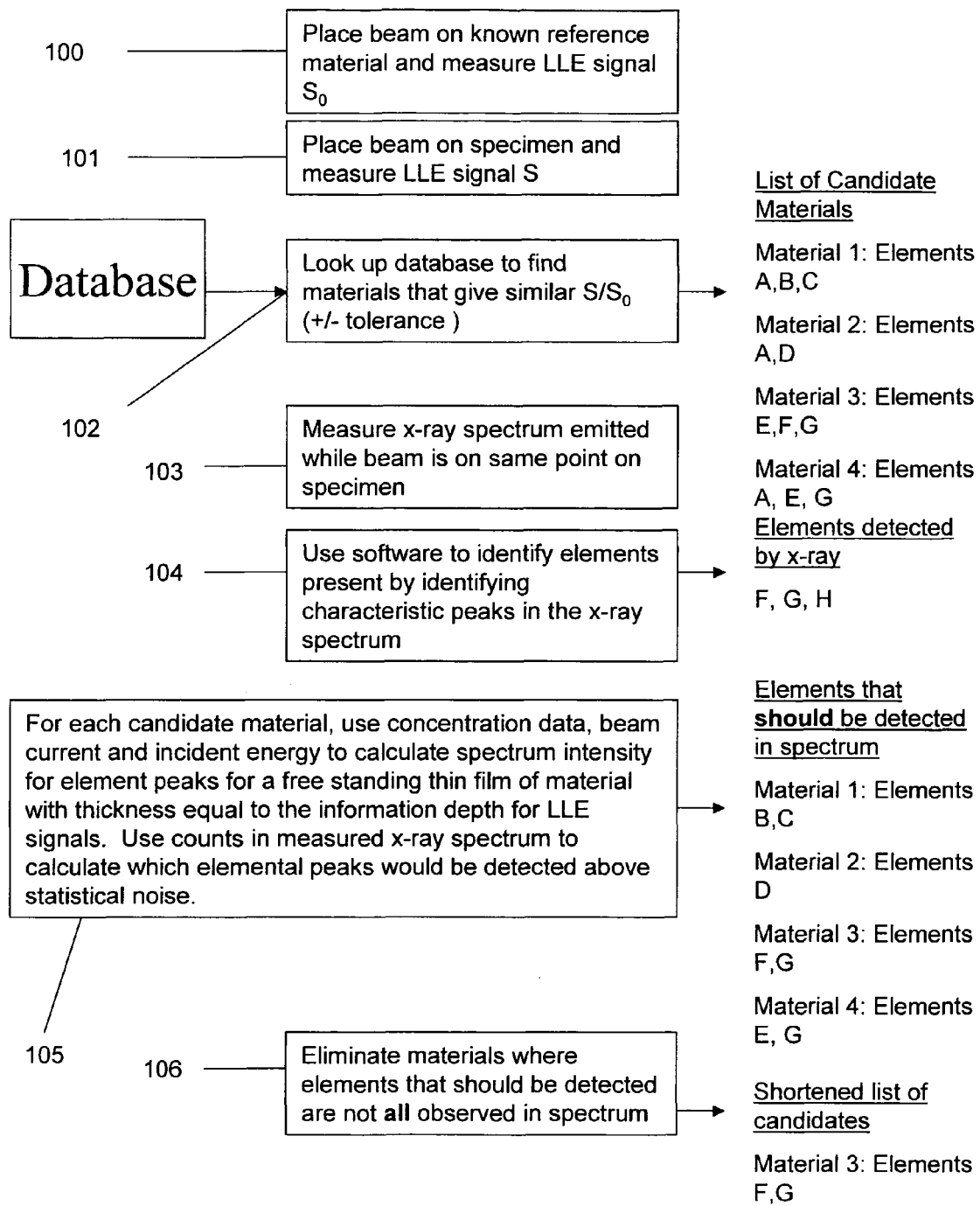
FIG. 5 is a flow diagram illustrating the selection of candidate materials using the method.

The procedure for combining LLE and x-ray information is described in more detail in association with FIG. 5 which is a flow chart showing how the x-ray signal is used to filter candidate materials identified by LLE signal. A comprehensive database of materials can be prepared, by experiment and/or by theory showing the effective atomic number Z and the composition of the material. This has been discussed earlier in association with FIG. 2. To analyse a small object at high resolution, the LLE signal is measured and converted to effective Z. The effective Z is then used to identify all candidate materials in the database that would give the same effective Z to within the experimental error of the measurement.

In FIG. 5, materials 1 to 4 have been identified as giving effective Z close to that observed from the LLE measurement. This involves, at step 100, placing the beam on a known reference material and measuring the LLE signal $S_0$. The beam is then placed on the unknown specimen and an LLE signal S is measured (step 101). A database is then queried for candidate materials that give a similar $S/S_0$ within a certain tolerance (step 102).

An x-ray spectrum is also obtained with the incident electron beam striking the object at the same point as for the LLE measurement (step 103). The spectrum is then processed by software to detect and identify elemental peaks at step 104 (elements F,G,H are identified in FIG. 5). Since electrons will invariably scatter beyond the object, the x-ray spectrum will contain contributions from the object and other materials in the immediate vicinity such as the substrate. For each candidate material in the database that would give a similar effective Z, the conservative test of detectability of elemental peaks is applied (step 105). In step 105, for each candidate material, concentration data, beam current and incident energy are used to calculate the spectrum intensity for element peaks for a free standing thin film of material with thickness equal to the information depth for LLE signals. Counts in the measured x-ray spectrum are then used to calculate which elemental peaks would be detected above statistical noise. If a peak should be seen yet there is no evidence of this in the x-ray spectrum, then that material is excluded from the candidates for the object at step 106.

In FIG. 5, materials 1, 2 and 4 are excluded because elements B,C,D, and E are not detected in the x-ray spectrum. Material 3 is the only candidate remaining and contains elements E,F,G therefore element H detected in the x-ray spectrum is from outside the small region generated the LLE signal. The elemental information from x-ray analysis is thus used to restrict the short list of candidates determined by LLE to help identify material composition at much higher spatial resolution than is possible by x-ray analysis alone. Thus analysis of very small objects, much smaller than 1000 nm in dimension, can be achieved.

Example 2

This second example describes the use of the invention in combination with a raster scan. If the incident beam is scanned over a raster covering a field of view, the LLE signal can be measured at each point in the raster and converted to an effective Z value. If this effective Z is plotted as a function of beam position, this will provide an image of the material in the field of view showing high resolution material contrast. If the same field of view is scanned while measuring the x-ray spectrum at each point, lower spatial resolution analytical information is obtained. U.S. Pat. No. 5,357,110 describes a method of combining the lower spatial resolution x-ray analytical information with an auxiliary signal such as a backscattered electron signal, to provide a composite image that shows analytical information of element content at the higher spatial resolution of the auxiliary signal.

We have realised that the same method can be used to combine the very high spatial resolution LLE image with the low resolution x-ray spectral image data. Thus, a high spatial resolution image can be obtained showing compositional detail at much less than 1000 nm spatial resolution. The techniques discussed in the context of the first example above can be used to implement this second example.

Example 3

This third example explains the use of the invention to obtain information upon layered structures.

Figure 6:
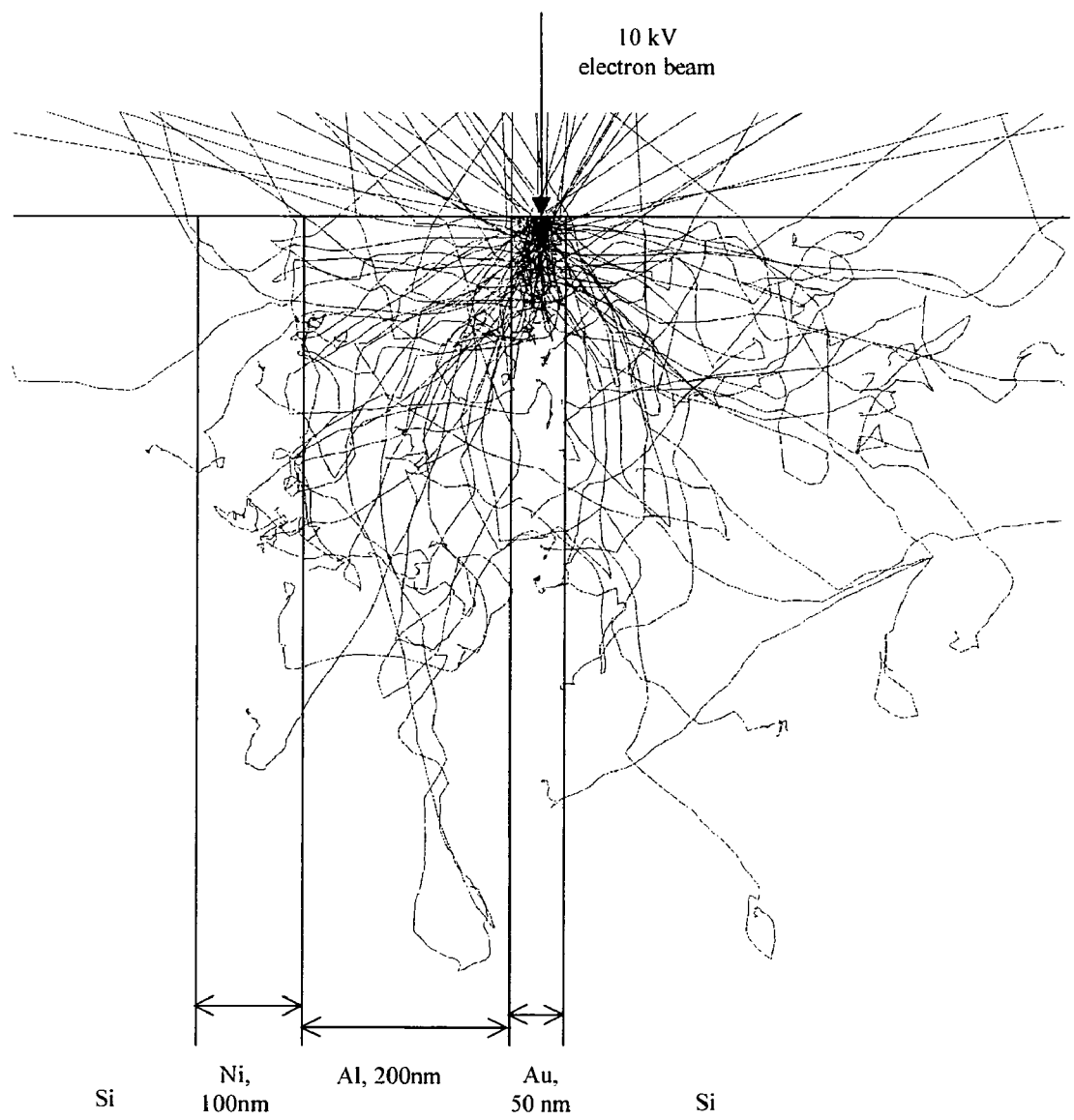
FIG. 6 shows the use of a method in relation to a multilayered specimen.

In this case the specimen consists of a number of layers of unknown composition and thickness. A vertical section can be prepared by focussed ion beam etching (FIB) in an SEM. The etched surface is presented normal to the incident electron beam (a 10 keV beam in this case). FIG. 6 shows a cross section illustrating the electron trajectories through such a specimen. In FIG. 6 the actual compositions of and thicknesses of the layers are shown, these being nickel (100 nm), aluminium (200 nm) and gold (50 nm), these all being sandwiched by a thick layer of silicon upon either side of the three layers.

When the focussed incident beam is within the Au layer, the LLE signal is generated by a small volume less than the layer thickness and is therefore representative of Au alone. However, the 10 keV incident electrons scatter within the specimen and excite x-rays from the neighbouring Ni, Al and Si. When such a sample is imaged by conventional raster scanning, or a line scan is obtained using the LLE signal, the location of the boundaries between layers can usually be seen from the contrasting signals from each layer. If two adjoining layers have very similar effective Z, then the junction between the layers is still usually visible in the secondary electron (SE) image using in SEM. Thus the thickness of the layer can be determined.

Within each layer, the high resolution LLE signal provides the effective Z but cannot determine the elemental content. However, x-ray spectra obtained with the incident beam on each layer provide information on the chemical elements present in all layers stimulated by the sideways scattered electrons and not just the layer under the beam. However, the two sources of information can be combined to find a self-consistent solution for the compositions of all the layers. This is now discussed further with reference to FIG. 7 and the flow chart in FIG. 8.

Figure 7:
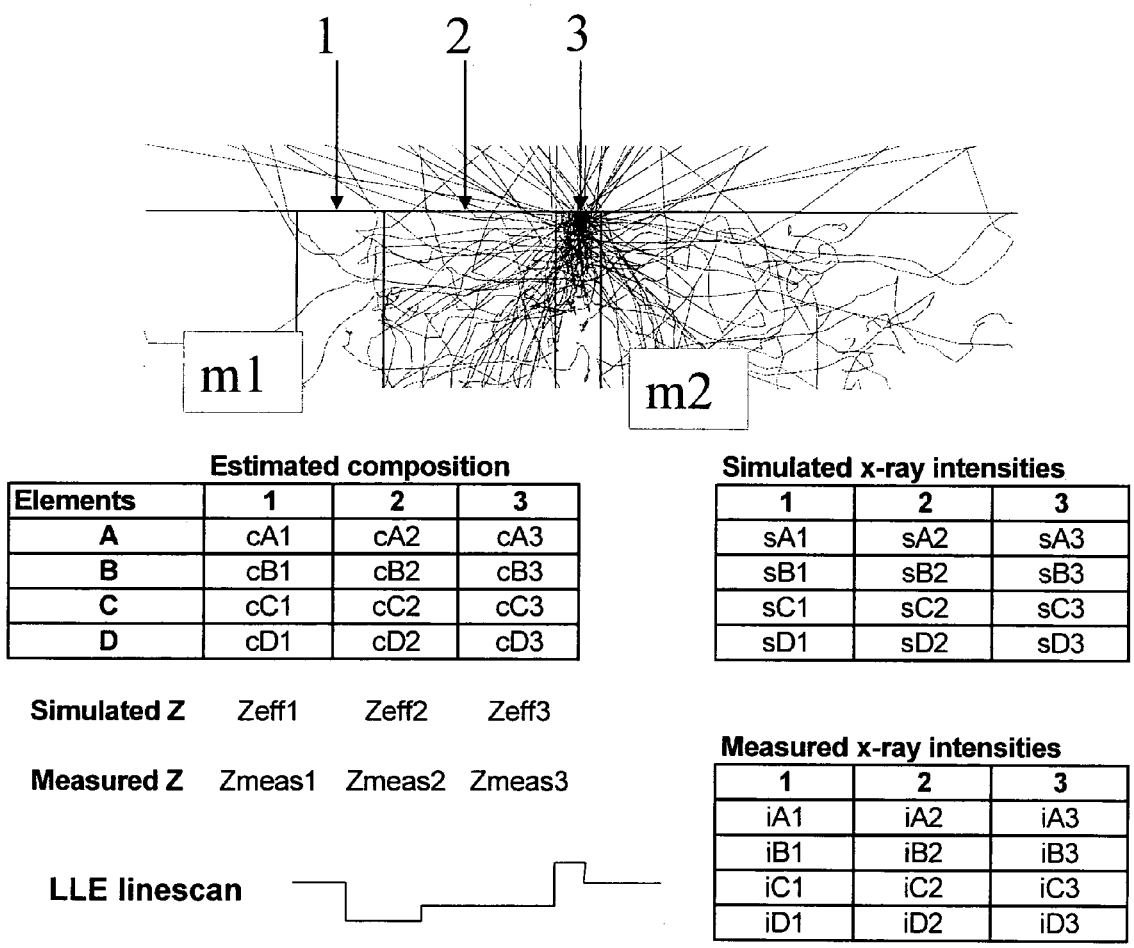
FIG. 7 shows a method related to FIG. 6 in more detail.

In FIG. 7 the LLE (or SE) line scan signal reveals the junctions of the various layers. With the incident electron beam at position 3, LLE is used to determine the effective Z ("Measured Z") for the material in layer 3, denoted "Zmeas3". X-ray signals for elements A,B,C,D are measured (iA3, iB3, iC3, iD3). The current estimated composition for layer 3 (cA3,cB3,cC3,cD3) is used to simulate the effective Z expected for layer 3, Zeff3. The current estimated compositions of all layers, and neighbouring matrix materials m1 and m2 (known) are used to simulate the x-ray intensities sA3, sB3,sC3,sD3. This is repeated with the incident beam at position 2 and position 1.

Figure 8:
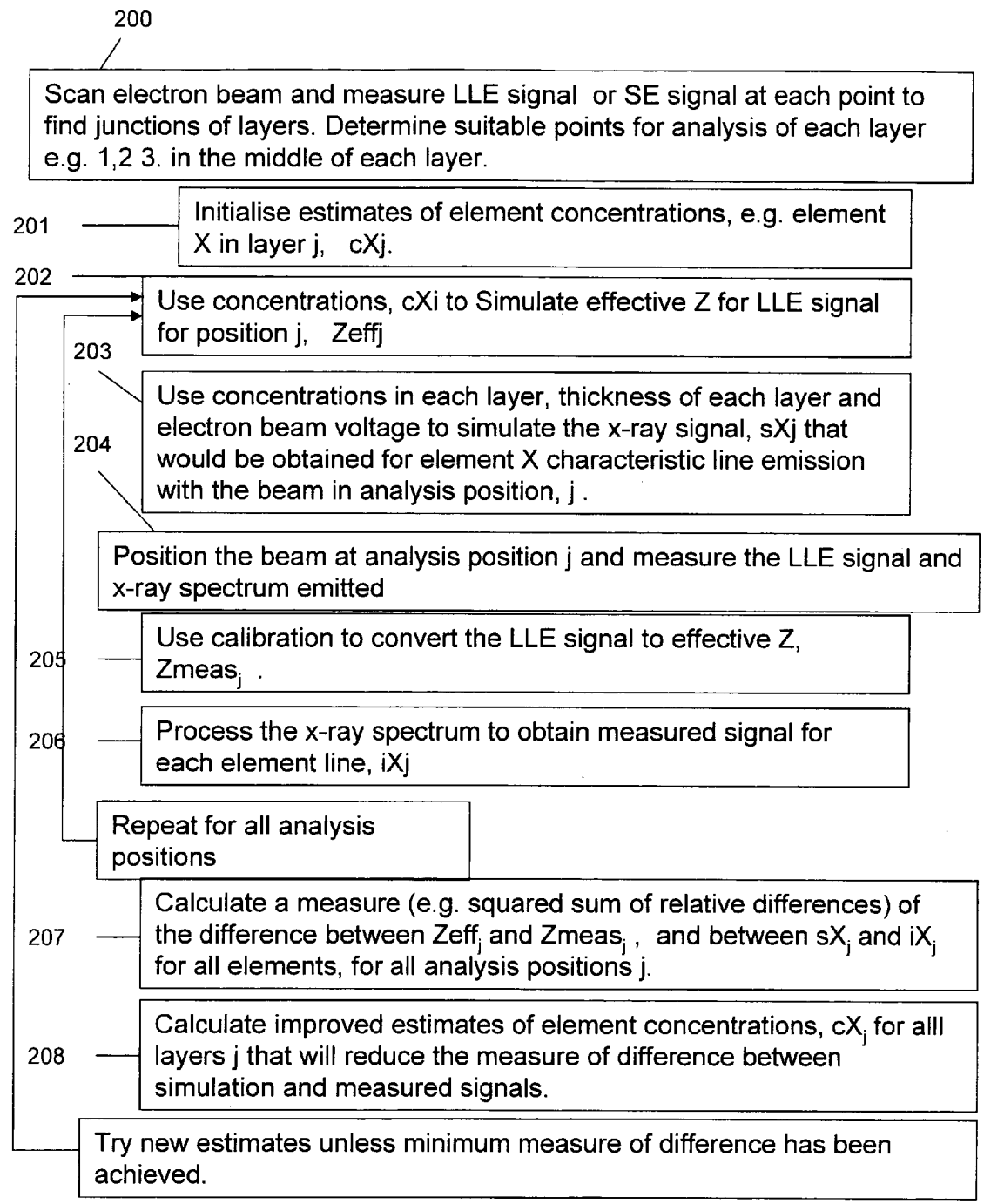
FIG. 8 shows a flow diagram relating to the method of FIGS. 6 and 7.

Referring now to FIG. 8 an initial step of finding the layer boundaries and using these to set analysis positions 1, 2, 3, . . . in the middle of each layer (see FIG. 7) is performed at step 200. At step 201, using the list of elements present, a first "guess" at a set of concentrations is made for each of the layers. This guess could simply be the apparent composition determined by x-ray analysis, accepting that this would include contributions from the neighbouring layers.

The set of concentrations for the elements in each layer is used to calculate the effective Z that would be expected from the LLE signal obtained with the beam on that layer at step 202. Then, at step 203, using the concentrations in each layer, the thickness of each layer and incident electron beam energy, the x-ray signal that would be obtained for each element characteristic line emission is simulated with the incident beam in the series of analysis positions 1, 2, 3, . . . , typically one at the middle of each layer.

Note that this simulation can be performed by a Monte Carlo trajectory modelling approach for example.

At step 204, with the beam at the series of analysis positions, the LLE signal is measured and an x-ray spectrum recorded in each case. The LLE signal is converted to an effective atomic number Z using a calibration curve (see FIG. 2 earlier) at step 205. The x-ray spectrum is also processed to obtain a measured signal for each elemental line within the spectrum (step 206). Steps 202 to 206 are repeated for each analysis position 1, 2, 3, . . . .

At step 207, the theoretical x-ray intensities are then compared with those measured in the observed x-ray spectrum at each point and the theoretical effective Z is compared with the measured effective Z. To do this, a figure of merit is calculated to describe how well the theoretical prediction matches the observed x-ray intensities. For example, this could be the sum of the squared relative differences between theoretical and measured values for all x-ray line signals and all effective Z signals.

The derived figure of merit from step 207 is then used in the selection of new estimates of the elemental concentrations for the layers (step 208).

The procedure of steps 202 to 208 is then performed repeatedly in an iterative cycle. In practice, there is no need to repeat the data acquisition at step 204 and saved data can be used within the iterative loop. The guessed compositions for the various layers are thus adjusted iteratively to improve this figure of merit until the best self-consistent solution is obtained for the structure and composition of the multilayer sample.

The iterative adjustment of composition is typically aided by using an approximate formula to express the lateral spread of the x-ray analytical information and using standard deconvolution methods on the spatial distributions for each element to correct for smearing of the information. The high spatial resolution LLE information on effective Z provides a strong constraint that enables the deconvolution of the x-ray data to be effective. Thus, quantitative elemental information for layers much less than 1000 nm in thickness can be obtained.

Example 4

The publication J. L. Pouchou. "X-ray microanalysis of stratified specimens", Analytica Chimica Acta, 283 (1993), 81-97 describes an SEM analysis technique for layered specimens using x-rays and which does not require FIB sectioning. In this fourth example we describe how this technique can be combined with the method of the present invention to improve upon the analysis process.

The specimen is typically presented normal to the incident electron beam and an x-ray detector is used to measure the intensities of the line emissions from elements present in the various layers of the specimen. If there is prior knowledge of the elements present in each layer, it is sometimes possible to find a self-consistent solution for the thicknesses of each layer and compositions of elements present in each layer by using a theoretical model for x-ray emission and an iterative solution method. However, in some cases, a solution is impossible to achieve using a spectrum obtained using a single beam energy. Whereas it is sometimes possible to obtain additional information from x-ray spectra at multiple incident beam energies to obtain a solution, each change in beam energy may alter the beam current and position of the incident beam and this makes multiple beam energy measurements difficult to achieve in practice. Therefore, it is highly desirable to perform the analysis using a single beam energy.

In order to excite x-ray lines from many elements, the SEM beam energy typically has to exceed 5 keV. However when the top layer (upon which the electron beam impinges) is less than 100 nm thick, x-rays are generated from both the top layer and the layers beneath. For an element that is present in the surface layer, the x-ray line intensity is affected by both the concentration of the element and the thickness of the layer. Whereas an increase in concentration would give higher intensity, this could also be produced by an increase in thickness. Therefore, a single measurement of line intensity for this element cannot resolve both the composition of the element and the thickness of the layer.

If all the elements in the layer emit x-ray lines that can be measured, then it is possible to find the relative concentrations of each element and use the normalisation condition that all concentrations must add up to unity in order to find a solution for the thickness of the layer. However, if there is one element that does not have a measurable line or one element is also present in the specimen beneath the surface layer, then it is not possible to apply the normalisation condition to resolve both composition and thickness of the surface layer.

It will be appreciated from the earlier discussion that the LLE signal is confined to a shallow surface layer and therefore the effective Z determined by LLE measurement is typically representative of the composition of the surface layer, but independent of the thickness. The equation relating elemental composition to effective Z provides an additional constraint on the composition of the surface layer that allows the thickness to be determined in some cases. The combination of LLE measurement and x-ray measurement thus offers an opportunity to measure both thickness and composition of thin surface layers using a single electron beam voltage.

Figure 9:
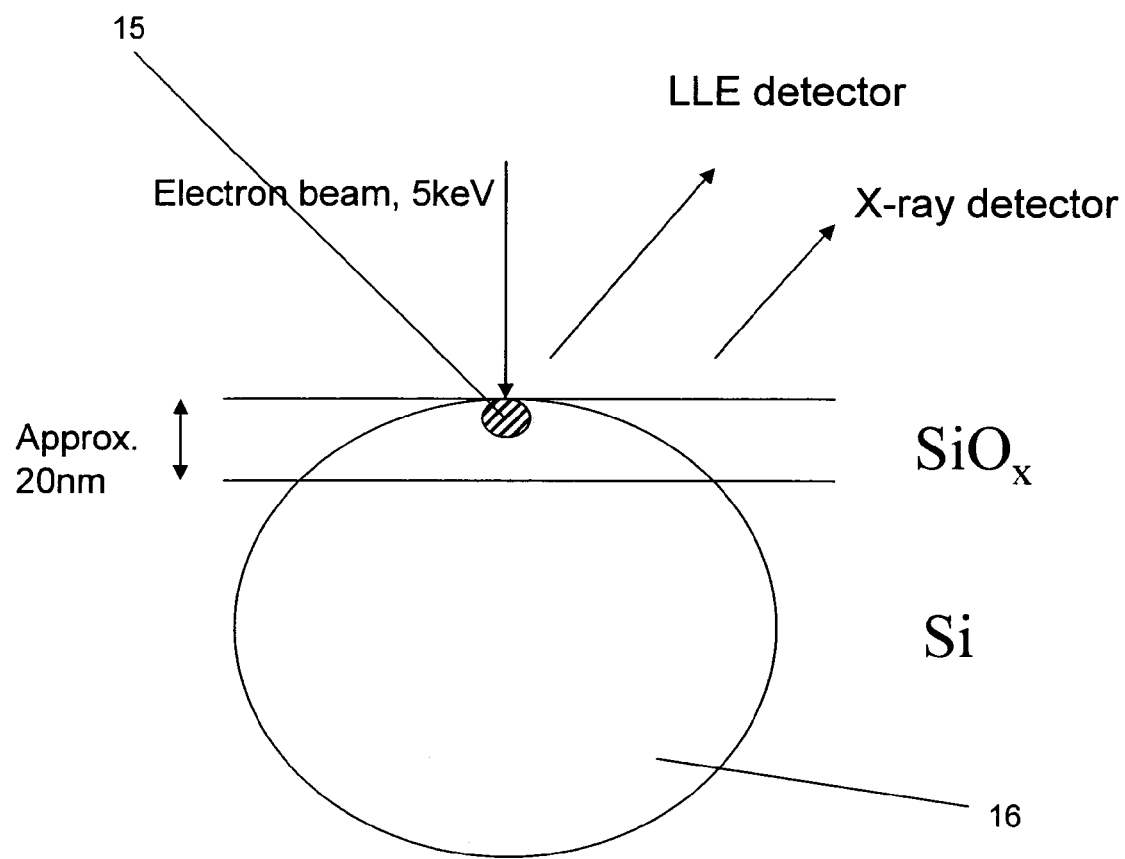
FIG. 9 shows the use of a method in relation to a silicon substrate covered with a silicon oxide layer; and, FIG. 10 shows an example arrangement of apparatus for performing the method.

FIG. 9 shows an example of this approach where it is desired to measure the thickness and composition of a layer of approximately 20 nm thickness of silicon oxide upon a silicon matrix. With a 5 keV incident electron beam, x-rays emerge from the large region 16. The silicon K intensity is a combination of the signal from the thin SiOx layer and the Si substrate and is similar to the intensity from a pure Si specimen so the Si signal does not give very useful information about the layer. The oxygen K intensity is directly affected by the thickness of the layer and also directly affected by the proportion of oxygen in the oxide. Therefore it is not possible to determine both the thickness and the composition with the oxygen K signal. However, the LLE signal with 50 eV loss is generated totally within the oxide layer and if the effective Z is determined from the LLE calibration, then the proportion of oxygen that would give the same effective Z can be determined. With the composition of the oxide determined by the LLE measurement, the thickness of oxide required to give the observed oxygen K x-ray intensity can then be determined using the x-ray signal.

Figure 1:
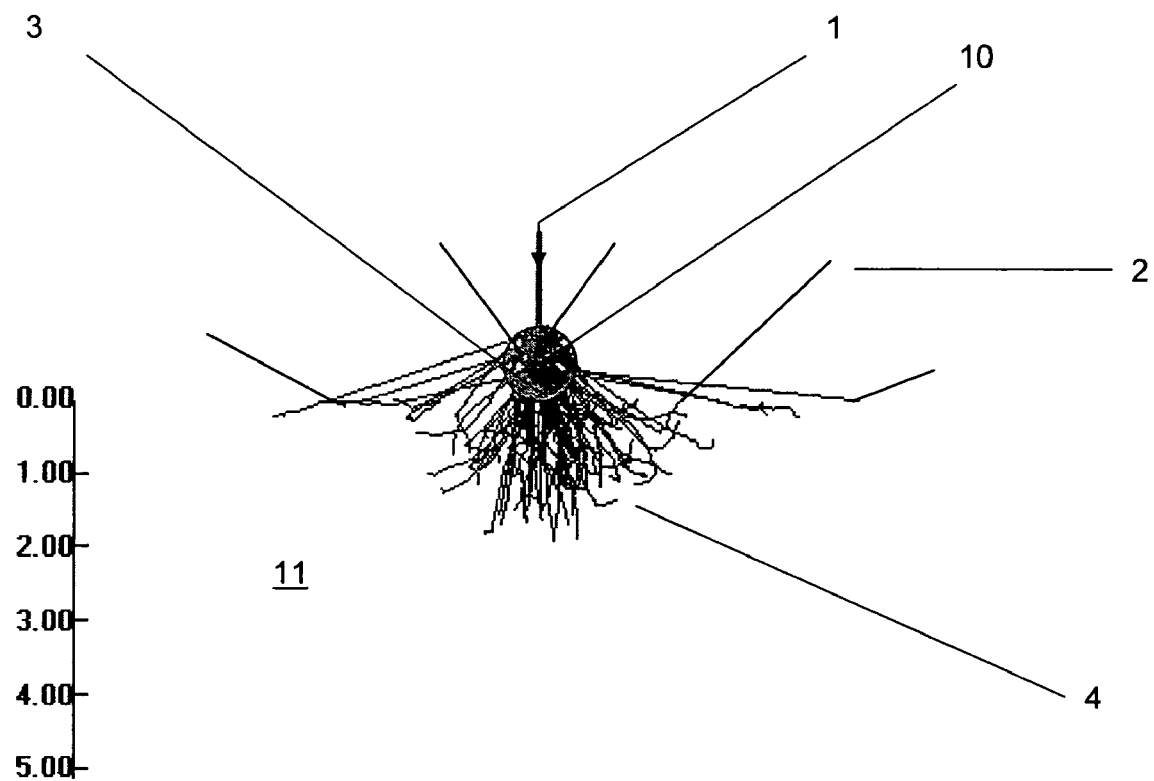
FIG. 1 shows the generation of backscattered electrons and x-rays as a result of electron beam incident upon a sample.

FIG. 1 shows the general arrangement of a apparatus suitable for implementing the invention, this illustrating the chamber of a scanning electron microscope. The microscope chamber generally indicated at 300 has an electron beam 1 which is incident upon a specimen 20. The incident beam consists of electrons that have been accelerated using a high voltage, this typically being 1 kV to 30 kV. This beam 1 is focussed through a set of electromagnetic lenses generally indicated at 21 so as to be incident upon the specimen 20. The electrons all strike the specimen with essentially the same energy. The specimen is typically earthed and incident electrons penetrate the specimen 20 and are scattered. The specimen 20 therefore emits electrons, together with x-rays, and these are each characteristic of the specimen 20, the measurement of their characteristics providing detailed information concerning the specimen material and structure as explained in the examples given above.

Figure 10:
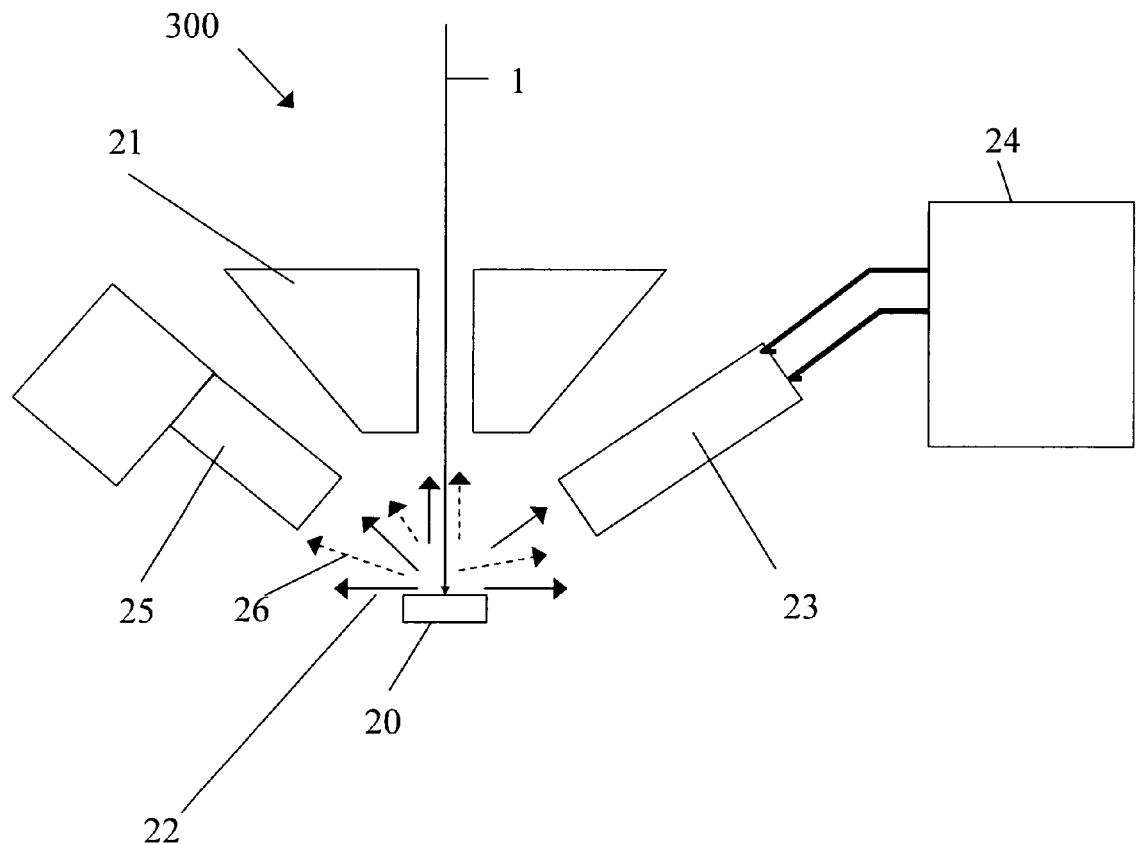

Typically electrons that are emitted from the specimen are emitted from a wide solid angle as indicated by the arrows 22 in FIG. 10. An electron analyser 23 is placed in the vicinity of the electron-emitting specimen 20. The electron analyser 23 is a retarding field analyser (RFA) which uses an electrostatic field to provide energy filtering of the emitted electrons which are gathered by the analyser. Typically such an electron analyser 23 is located to one side of the electron beam 1. The analyser is typically connected to a process and control system 24 which controls the operation of the analyser and provides detection electronics so as to obtain a signal which is characteristic of the received electrons. As can be seen in FIG. 10, a second detection device in the form of an x-ray detector 25 is positioned also adjacent the specimen 20 for detecting x-rays emitted from the specimen. This is positioned on another side of the electron beam 1 and is likewise in communication with the control system 24 (not shown). Emitted x-rays are generally indicated at 26 in FIG. 1. The control system is operated by an SEM computer (not shown) upon which conveniently (although not essentially) the calculations can be performed in the implementation of the invention.

The invention therefore provides a number of significant advantages over methods and apparatus according to the prior art, some of these being:—
  a) Use of LLEs rather than backscattered electrons delivers a spatial resolution typically an order of magnitude better that that presently known in the art.
  b) Use of LLEs rather than backscattered electrons allows the composition of small objects to be studied without having to measure the object and apply a correction for the object size, or the substrate.
  c) The possible use of a detector that counts individual electrons independent of their energy, rather than measuring the aggregate conversion current (that is the standard method of measuring backscattered electrons), avoids problems of offset and gain drift and allows the theoretical yield to be predicted without knowledge of the energy transfer function of the detector.
  d) LLE data offers low detail quantitative analytical information with a small information volume. X-ray data offers detailed quantitative elemental information with a large information volume. Combining these two provides an analytical technique that can deliver quantitative elemental information from a small information volume and thus analyse much smaller objects. This is critically important for semiconductor defect review for example, where significant defects are well below 100 nm in dimension and for nanotechnology applications where film thicknesses and object dimensions are also well below 100 nm.

The invention claimed is:

1. A method for quantitative analysis of a material in which an electron beam is caused to impinge upon the material, the method comprising:
  detecting low loss electrons (LLEs) that have been backscattered from a first region of the material due to interaction with the electron beam and generating corresponding LLE data;
  detecting x-rays received from a second region of the material due to interaction with the electron beam and generating corresponding x-ray data, wherein the first and second regions overlap; and
  analysing the LLE data together with the x-ray data so as to generate compositional data representative of the composition of the first region.

2. A method according to claim 1, wherein the first region is contained within and is substantially smaller in volume than the second region.

3. A method according to claim 1, wherein the energy of the low loss electrons is at least 80 percent of those within the electron beam.

4. A method according to claim 1, wherein the analysing step comprises processing the LLE data to obtain an effective atomic number representative of the element or elements within the first region.

5. A method according to claim 1, further comprising selecting a candidate material from a number of possible candidate materials for the first region, based upon the LLE data.

6. A method according to claim 5, further comprising calculating simulated x-ray data for the candidate material, the simulated x-ray data being that which is received only from the first region.

7. A method according to claim 6, wherein the simulated x-ray data and the x-ray data are compared so as to determine which elemental contributions to the x-ray data from the first region are detectable within the x-ray data.

8. A method according to claim 7, further comprising, repeating the method for a number of different selected candidate materials and forming a set of candidate materials having corresponding compositional data wherein, if one or more elemental contributions should be detectable but are not present within the x-ray data for a particular candidate material then the said particular candidate material is not included within the set.

9. A method according to claim 5, further comprising analysing the x-ray data so as to identify elements present within the second region; selecting a number of candidate materials for the first region based upon the LLE data wherein the candidate materials each comprise a number of elements; comparing the common elements identified from the x-ray data and the candidate materials; and ranking the candidate materials in accordance with the comparison.

10. A method according to claim 1, further comprising causing relative movement between the electron beam and the material so as to obtain LLE data and x-ray data from a number of different locations and performing the method at each said location, wherein the different locations are arranged to collectively form a field of view region, and wherein the method further comprises forming image data representative of the compositional data at each location.

11. A method according to claim 10, wherein the material comprises a plurality of layers and wherein the incident electron beam is arranged approximately parallel to the surfaces of the layers.

12. A method according to claim 11, further comprising, iteratively:
   i) defining composition data for each layer;
   ii) using the composition data to calculate the effective atomic number for each layer;
   iii) simulating the x-ray emission as simulated x-ray data from at least one electron beam position for each layer;
   iv) detecting the low loss electrons and x-rays for each electron beam position;
   v) comparing the detected and simulated x-ray data;
   vi) calculating an effective atomic number based upon the detected LLE data;
   vii) comparing the calculated effective atomic number in step (v) with that of step (ii);
   viii) adjusting the composition data and repeating steps (i) to (vii) using the adjusted composition data as the defined composition data, until the difference between the results of each comparison reaches a predetermined threshold.

13. A method according to claim 1, wherein the material comprises a number of layers and wherein the incident electron beam is arranged approximately normal to the said layers, such that it is incident upon a first of the plurality of layers.

14. A method according to claim 13, wherein the method is used to obtain the composition of the first layer.

15. Apparatus for performing quantitative analysis of a material, the apparatus comprising:
   an electron beam generator which in use causes an electron beam to impinge upon a sample of the material;
   a low loss electrons (LLE) detector positioned so as to receive and detect low loss electrons from a first region of the material due to interaction with the electron beam, the low loss electrons detector producing a corresponding LLE signal;
   an x-ray detector positioned so as to receive and detect x-rays from a second region of the material due to interaction with the electron beam, the x-ray detector producing a corresponding x-ray signal; wherein the first and second regions overlap; and,
   a processor adapted to analyse LLE data representative of the LLE signal, together with x-ray data representative of the x-ray signal, so as to generate compositional data representative of the composition of the first region.

* * * * *